United States Patent [19]

Mundschenk

[11] Patent Number: 5,512,278
[45] Date of Patent: Apr. 30, 1996

[54] OINTMENT BASE USEFUL FOR PHARMACEUTICAL PREPARATIONS

[75] Inventor: David D. Mundschenk, Dania, Fla.

[73] Assignee: PhyloMed Corporation, Plantation, Fla.

[21] Appl. No.: 180,078

[22] Filed: Jan. 11, 1994

[51] Int. Cl.$^6$ ..................................................... A61K 31/74
[52] U.S. Cl. ........................ 424/78.06; 424/616; 514/900; 514/902
[58] Field of Search ................................ 424/78.06, 616; 514/900, 902

[56] References Cited

U.S. PATENT DOCUMENTS

| | | |
|---|---|---|
| 3,526,682 | 9/1970 | Timreck . |
| 4,711,783 | 12/1987 | Huc . |
| 4,766,012 | 8/1988 | Valenti . |
| 4,980,154 | 12/1990 | Gordon . |
| 5,000,886 | 3/1991 | Lawter . |
| 5,066,436 | 11/1991 | Komen . |
| 5,145,604 | 9/1992 | Neumiller . |

*Primary Examiner*—Shean C. Wu
*Attorney, Agent, or Firm*—Fredrikson & Byron

[57] ABSTRACT

An ointment base useful for preparing topically applied medicament formulations. The base can be provided in the form of a stable emulsion including paraffin(s), polyol, beeswax, cetostearyl alcohol, a 4-hydroxy benzoic acid lower alkyl ester, a surface active agent and a dispersing agent. The base can be combined with large volumes containing a variety of medicaments to form stable, useful formulations.

16 Claims, No Drawings

OINTMENT BASE USEFUL FOR PHARMACEUTICAL PREPARATIONS

TECHNICAL FIELD

The present invention relates to dermatological vehicles including ointments and other topical preparations and formulations useful for the delivery of medicaments.

BACKGROUND ART

Medicaments can be dispensed in a wide variety of vehicles and forms, including powders, capsules, liquids, aerosols, and the like. Medicaments for dermatological use can be provided in liquid or solid form. More typically, dermatological formulations are provided in semisolid form as lotions, creams, ointments, pastes, liquids, plasters, and poultices.

Microencapsulated preparations have been described as useful for a variety of purposes, including for the delivery of dentifrice compositions and pharmaceuticals. See, e.g., U.S. Pat. Nos. 3,526,682, 4,711,783, 4,766,012, 4,980,154, 5,000,886, and 5,066,436. Similarly, U.S. Pat. No. 5,145,604 describes an aqueous emulsion system containing vesicular structures as a delivery system for a variety of active ingredients.

The cosmetic and pharmaceutical industries typically prepare dermatological formulations in ready-to-use form. In other words, it is common to tailor-make an ointment or other vehicle for use with a particular type and amount of a medicament, combine the two, then package and sell the resulting formulation.

It would often be desirable, however, to allow pharmacists or end-users of medicated ointments to prepare their own formulations, using ready-made or previously prepared ointment bases or concentrates. This generally requires, however, that a user have access to the materials and methods, as well as instructions, that would allow him or her to prepare an effective formulation on a medicament-by-medicament basis.

There presently appear to be few, if any, commercially available medicament bases that can be prepared in advance and used with a wide variety of solutions and medicaments, particularly in a manner that can accommodate a wide range of added volumes and types of medicaments.

SUMMARY OF THE INVENTION

The present invention provides an ointment base that can be used as a vehicle for a wide variety of medicaments and with a broad range of medicament volumes and concentrations. The ointment base of the present invention is prepared using a combination of commonly available ingredients identified as "generally recognized as safe" ("GRAS").

In particular, the invention provides an ointment base for preparing topically applied medicament formulations, comprising a stable emulsion of at least about 10% by weight of each of water, one or more paraffins, and a liquid polyol; and less than about 10% by weight of each of beeswax, cetostearyl alcohol, a 4-hydroxy benzoic acid lower alkyl ester, a surface active agent, and a dispersing agent.

In a preferred embodiment, the paraffin component includes both liquid paraffin and soft paraffin (white petrolatum), the liquid polyol component is glycerol, the beeswax component is white beeswax, the 4-hydroxy benzoic acid lower alkyl ester component is methyl parabens, the surface active agent is polyoxyethlenesorbitan monostearate (e.g., "Polysorbate 60" or "Tween 60"), and the dispersing agent is glyceryl monostearate.

The ointment base of the present invention can be easily prepared and can be stably stored for long periods of time at room temperature. In order to prepare a medicament formulation, the ointment base can be combined with a suitable volume of a medicament-containing solution, e.g., up to 50% by weight of the final formulation. With suitable mixing, the ointment base appears to "microencapsulate" the added solution within water or oil based particulate phases of the ointment, thereby forming a stable suspension of microspheres.

According to the present invention there is further provided a pharmaceutical formulation useful for the microencapsulation of medicaments, the formulation comprising:

(a) between about 50% and about 99% by weight of an ointment base as described herein, based on the weight of the formulation, and (b) between about 50% and about 1% of a medicament, preferably in the form of a medicament-containing solution.

In a preferred embodiment, other adjuvants such as hydrogen peroxide and other antimicrobial agents can be incorporated into the formulation. Such adjuvants are released in situ over time in a manner that serves to protect the surrounding tissue from damage caused by oxidation and irritation.

The ointment base of the present invention provides the unique ability to prepare and use medicament formulations in two distinct steps, namely, a first step in which the vehicle ointment base itself can be prepared and stably stored, and a second step in which a medicament-containing solution can be combined with a portion of the vehicle ointment base.

DETAILED DESCRIPTION

The present invention provides an ointment base that can be used as a vehicle for a wide variety of medicaments, in order to prepare topically applicable formulations containing such medicaments in an efficacious, time-release manner. As used herein, the term "ointment base" will refer to the stable mixture of ingredients of the final formulation other than the medicament solution. The word "formulation", as used herein will refer to the combination of ointment base and one or more medicament solutions. Lastly, the term "medicament solution" will refer to the active agent or other agent to be delivered dermatologically, in whatever vehicle or form it is used to combine it with ointment base.

While not intending to be bound by theory, microscopic examination suggests that upon combining the ointment base with a medicament solution, the resulting formulation forms a stable emulsion having droplets within which the medicament solution is spontaneously encapsulated within the ointment base.

A preferred ointment base of the present invention preferably comprises the following ingredients:

(1) at least about 10% by weight of each of water, one or more paraffins, and a liquid polyol;

(2) less than about 10% by weight of each of beeswax, cetostearyl alcohol, a 4-hydroxy benzoic acid lower alkyl ester, a surface active agent, and a dispersing agent.

In a preferred embodiment, the paraffin component includes both liquid paraffin and soft paraffin (white petrolatum), the liquid polyol component is glycerol, the beeswax component is white beeswax, the 4-hydroxy benzoic acid lower alkyl ester component is methyl parabens, the surface active agent is polyoxyethlenesorbitan monostearate, and the dispersing agent is glyceryl monostearate.

The paraffin component is present in a total amount of at least about 10%, and preferably at least about 12%, by weight of the ointment base. The paraffin ingredient preferably comprises liquid paraffin, present in an amount between about 3% and 8%, and most preferably between about 4% and 6% by weight of the ointment base. The paraffin ingredient preferably further comprises white petrolatum, also known as "soft paraffin", in an amount preferably between 5% and 15%, and most preferably between 8% and 12% by weight of the ointment base.

The polyol component of the preferred ointment base comprises glycerin (also known as glycerol) as a water-miscible cosolvent that can serve as a humectant in order to withdraw moisture from the skin. Glycerol is generally included at a concentration between about 20% and about 45%, and preferably between about 25% and about 35%, by weight of the ointment base.

The ointment base of the present invention further comprises beeswax, and preferably "white" beeswax, present in a concentration of between about 0.1% and 1.0%, preferably between about 0.3% and 0.5% by weight of the ointment base.

The ointment base further comprises cetostearyl alcohol in an amount between about 6% and about 10%, and preferably between about 7% and about 9% by weight of the ointment base. Cetostearyl alcohol is a mixture chiefly of hexadecyl and octadecanyl alcohols, and is commercially available in forms suitable for use in ointments.

The ointment base further comprises a 4-hydroxy benzoic acid lower alkyl ester ("parabens") as a preservative. A preferred parabens is methyl paraben (i.e., p-hydroxybenzoic acid methyl ester), present in an amount between about 0.1% and about 0.5%, and preferably between about 0.3% and about 0.4% by weight of the ointment base.

The ointment base further comprises a surface active agent, preferably from the class known as polyoxyethylene sorbitan esters. Such surface active agents are preferably present at a concentration of between about 1% and about 10%, and more preferably between about 2% and about 5%, by weight, based on the weight of the ointment base. Those esters commonly known as "Polysorbates", or in the alternative "Tweens", are preferred. Particularly preferred is Polysorbate 60, a polyoxyethylene sorbitan ester having a fatty acid composition of about 50% stearic acid (polyoxyethylenesorbitan monostearate) and the balance primarily palmitic acid.

Lastly, the ointment base of the present invention further comprises a dispersing agent, preferably in the form of glyceryl monostearate. Glyceryl monostearate is preferably present in an amount between about 0.5% and about 5%, and preferably between about 1% and about 3% by weight of the ointment base. A suitable form of glyceryl monostearate is available commercially, for instance, under the tradename "Imwitor 960".

To the combined components described above is added purified water, as described in greater detail below.

One example of a particularly preferred ointment base, therefore, is a composition that comprises the following ingredients:

|  | Weight % |
| --- | --- |
| Liquid paraffin | 5 |
| White petrolatum | 10 |
| Glycerin | 30 |
| White beeswax | 0.4 |
| Cetostearyl alcohol | 8 |
| Methyl paraben | 0.3 |
| Polyoxyethylenesorbitan monostearate | 3.6 |
| Glyceryl monostearate | 2 |
| Purified water | to 100 |

Ointment bases of the present invention can be prepared in any suitable manner, using techniques and equipment within the skill of those skilled in the art. The preferred ointment base identified above was prepared as follows:

STEP I - Preparation of Water Phase

Purified water, Polysorbate 60, and glycerin were added with agitation to a standard laboratory mixing kettle ("Korvina" brand). The contents were heated to 63°±2° C. Methyl paraben was added, and the composition was mixed to dissolve this ingredient while maintaining temperature at 63°±2° C.

STEP II - Preparation of Oil Phase

In a suitable vessel liquid paraffin, cetostearyl alcohol, white petrolatum, glycerol monostearate (Imwitor 960), and white beeswax were combined and were continuously mixed as the composition was heated to 73°±2° C.

STEP III - Mixing of Phases

The mixture of Step II was transferred to the side feed container of the Korvina kettle, with the water phase maintained under 300 millibar vacuum. With mixing, and keeping the temperature at 63°±2° C., the oil phase was drawn into the water phase. The resulting composition was mixed for 15 minutes with agitation and vacuum at 300 millibar and 63°±2° C. While mixing and under vacuum, the mixture was allowed to cool to 40°±2° C., then was allowed to continue cooling with agitation to 33°± 2° C. The mixture was finally cooled to room temperature, whereupon the vacuum was released, and the resulting ointment base was packaged in bulk.

The ointment base of the present invention can be used as a vehicle, e.g., an encapsulating medium, for a variety of medicaments. Suitable medicaments include any compound, solution or molecule that is desired to be delivered to the body or applied to the skin by means of a topical, sustained delivery mechanism. Examples of medicaments that can be delivered to the body by such a topical delivery route include topical analgesics, anesthetics, antibacterials, antibiotics, antifungal agents, anti-inflammatory agents (such as salicylates and steroids), antineoplastics, antiparasitics, antipruritics, antiviral agents, biologicals, contraceptives, dental preparations, deodorants, enzymes and digestants, germicides, hemorrhoidal preparations, hormones, minerals, vaginal preparations, and the like.

In a preferred embodiment, the ointment base of the present invention is used for the preparation of dermatological preparations useful as topical preparations for the application of abradants, antiacne preparations, antibacterials and/or antifungals, antidermatitis preparations, as well as antiherpes, anti-inflammatory, antiperspiration, antipruritics, antipsoriasis, antiseborrhea, or astringent agents; coal tar, depigmenting agents, detergents, emollients, fungicides, keratolytics, moisturizers, pediculicides, photosensitizers, scabicides, skin bleaches, skin protectants, cleansers, steroids, sulfur and salicylic acid, sun screens, vesicants, wart therapeutic agents, wound dressings, and the like.

Examples of particularly preferred medicaments include purified sea water, pharmaceutically-active agents, amino acids, peptides, proteins such as fibrous proteins and globular proteins, enzymes, vitamins, carbohydrates, lipids (such as fatty acids, di- and triacylglycerols), nucleotides, oligonucleotides, hormones, milk proteins, herbal extracts, and perfumes.

Examples of preferred suitable medicaments (and their intended use) include the following: (percentages are provided on a weight basis, based on the weight of the final formulation)

sodium chloride (e.g., about 0.9%), for use in treating cold sores and fever blisters and lesions associated with Herpes virus;

hydrogen peroxide (e.g., about 1% to about 15%, preferably about 8% to about 12%), as an anti-infective cream for use in the oral cavity or topically for minor wounds (See, for instance, U.S. Pat. Nos. 4,983,379, 5,039,515 and 5,208,010, the disclosures of which are incorporated herein by reference);

EDTA (ethylenediaminetetracetic acid), sorbitol (D-glucitol), sodium tosyl chloride (p-toluenesulfonyl chloride), benzalkonium chloride, or allantoin, (any of which may further include aspartame and artificial flavor as desired), for use in anti-infective creams useful in the oral cavity or topically for minor wounds;

sodium salt of Acyclovir™ (e.g., 0.5% solution), as an anti-infective topical antiviral cream for use on the skin and lips;

nicotinamide solution (e.g., 10%), as a topical preparation for use on pre-cancer skin lesions;

glutathione (e.g., 50%, by weight), as an oral delivery system for glutathione; and uridine 5'-diphosphoglucose ("UDPG"), e.g., 20 grams for oral delivery.

In a particularly preferred embodiment, one or more peptides can be included as the medicament, the peptides having been previously oxidized by the use of an oxidizing agent such as performic acid. Examples of such peptides include collagen and elastin. The use of such chemically modified peptides is believed to itself be novel in the cosmetic industry. The peptides are particularly useful since they are not themselves affected by oxidation. Formulations containing such modified peptides can be used to activate fibroblast cells that in turn serve to produce matrix proteins necessary for wound healing.

The ability of such processed proteins to "condition" cells is exemplified by the ability of such proteins to soften the skin and increase its elasticity. Such effects can be seen over time when a product of the present invention is used periodically, e.g., twice a day for 10–14 days. In use, the ointment base of the present invention is typically, and preferably, prepared in advance and is allowed to stabilize at room temperature. A solution containing the medicament of choice can thereafter be added to the ointment base using standard mixing and blending techniques. While medicaments can be added in any suitable manner, e.g., in powder form, medicaments are preferably first solubilized or otherwise dispersed in a solution, and the resulting medicament solution is then combined with ointment base in order to prepare a formulation.

Suitable solvents for use in preparing a medicament solution of the present invention are those that provide an optimal combination of such properties as: the ability to solubilize the desired medicament; compatibility with the ointment base; and suitability for topical use. An example of a particularly preferred solvent is water. Typically, a medicament solution is slowly added to the ointment base under continuous mixing, using standard paddle mixers as are typically employed in the manufacture of topical creams and ointments.

Medicament solutions can be added in amounts from about 1% to about 50%, by weight, based on the weight of the final formulation.

The ointment base of the present invention is particularly useful for preparing formulations containing a plurality of different medicaments. Such formulations can be prepared, for instance, by preparing individual formulations of the medicaments, and then combining the resultant single-medicament formulations with each other in a desired manner and concentration.

Particularly preferred is a formulation that contains both hydrogen peroxide (as an anti-infective agent) and glycerin (as a skin or tissue protectant). The combination of hydrogen peroxide and glycerin has been used as effective local therapy for the treatment of pharyngitis, laryngitis, thrush, gingival infection and necrotizing ulcerative gingivitis. The combination, being non-toxic, is effective as a wide spectrum antibacterial and antifungal agent. When used for treating bacterial infections, the combination provides symptomatic relief and serves as an adjunct to systemic therapy. It also relieves pain associated with these conditions, thereby enabling the patient to maintain or resume normal oral intake. The combination cleanses the tissue of debris, soothes irritated tissues and aids in restoring good oral hygiene. Patient acceptance has been good. See, for instance, Williams, J. C.; Topical Therapy in Infections of the Mouth and Pharynx, *Med Times,* 91:332–334 (1963).

Glycerin is quite effective in protecting the skin and mucous membranes of the mouth and oral cavity. FDA monographs, for instance, define glycerin as an "Active Skin Protectant" for use on skin, lips, and the oral cavity.

Similarly, hydrogen peroxide, for instance at a 3% concentration, has been used extensively as a tooth whitener. Such beneficial uses of hydrogen peroxide include its use as an oral germicide, cleansing agent and hemostat. It is considered a useful disinfectant for mucous membranes because of its low toxicity. See, e.g., Zinner. D. D., et. al.; Controlled Study of the Clinical Effectiveness of A New Oxygen Gel on Plaque. Oral Debris and Gingival inflammation, *Pharmacol. Ther. Dent.,* October 1970, 1:7–15. Eighty subjects who used peroxide gel for chronic gingival inflammation showed no evidence of untoward side effect on the gingival and mucosa of the tongue, cheeks or on the dentition. There were no observable side effects in any of the subjects. The mixture was used on the teeth and gingiva for two minutes, twice daily after tooth brushing as part of a daily oral hygiene program. (Shapiro. W. B., et. al.: The Influence of Ureo Peroxide Gel on Plaque, Calculus and Chronic Gingival Inflammation, *J. Perigdont,,* 44(10):636–639 (1973)).

It does not appear, however, that commercial products incorporating hydrogen peroxide as a tooth whitener also attempt to protect the gums and buccal membranes. Formulations of the present invention therefore provide a unique combination of the beneficial applications of hydrogen peroxide as well as protection of sensitive tissue in the mouth and gums.

The ointment base of the present invention is stable in storage; e.g., it can be stored one or more years without noticeable affect on its desired properties. It is preferably stored in a closed container and at room temperature.

The present invention will now be described with reference to various embodiments thereof. It will be apparent to those skilled in the art that many changes can be made in the embodiments described without departing from the scope of the present invention. Thus the scope of the present invention should not be limited to the formulations described in this application, but only by formulations described by the language of the claims and the equivalents of those formulations.

EXAMPLES

EXAMPLE 1

Preparation of Ointment Base and Formulations

An ointment base according to the present invention was prepared having the following ingredients:

|  | Weight % |
| --- | --- |
| Liquid paraffin | 5 |
| White petrolatum | 10 |
| Glycerin | 30 |
| White beeswax | 0.4 |
| Cetostearyl alcohol | 8 |
| Methyl paraben | 0.3 |
| Polyoxyethylenesorbitan monostearate | 3.6 |
| Glyceryl monostearate | 2 |
| Purified water | to 100 |

The ointment base was prepared as follows:

STEP I - Preparation of Water Phase

Purified water, Polysorbate 60, and glycerin were added with agitation to a mixing kettle ("Korvina" brand). The contents were heated to 63°±2° C. Methyl paraben was added, and the composition was mixed to dissolve this ingredient while maintaining temperature at 63°±2° C.

STEP II - Preparation of Oil Phase.

In a suitable vessel liquid paraffin, cetostearyl alcohol, white petrolatum, glycerol monostearate (Imwitor 960), and white beeswax were combined and were continuously mixed as the composition was heated to 73°±2° C.

STEP III

The mixture of Step II was transferred to the side feed container of the Korvina kettle, with the water phase maintained under 300 millibar vacuum. With mixing, and keeping the temperature at 63°±2° C., the oil phase was drawn into the water phase. The resulting composition was mixed for 15 minutes with agitator and vacuum at 300 millibar and 63°±2°. While mixing and under vacuum, the mixture was allowed to cool to 40°±2°, then was allowed to continue cooling with agitation to 33°±2°. The mixture was finally cooled to room temperature, whereupon the vacuum was released, and the resulting ointment base was packaged in bulk.

The ointment base was used as a vehicle for a variety of medicaments, including the following, each of which was added to the ointment base at a ratio of 1 part medicament to 2 part base; purified sea water, pasteurized milk, egg products, various herbal mixtures, aloe vera, and various fragrances.

EXAMPLE 2

Preparation of Dental Cream

Hydrogen peroxide dental cream for use in cases of gingivitis and other dental conditions was prepared by adding an anti-infective agent (3% hydrogen peroxide) to an ointment base prepared as described in EXAMPLE 1 above, although having 20% rather than 30% glycerin by weight. The cream format was found to provide a slower, more prolonged release of peroxide than is typically seen with conventional liquid formats.

An extended clinical study was conducted involving 464 dental patients. The dental cream was dispensed for each patient. The cream was applied either as a topical ointment, usually for the treatment of a specific condition in the mouth or lip, or was dosed by tooth brushing for conditions such as gingival infection, irritation or chronic/acute gingivitis. Subjects were initially provided with two ½ ounce jars of the cream, an amount sufficient for a two week period.

Positive results were seen in over 90% of the patients initially having gingivitis, bleeding gums, swelling, irritation and redness.

The cream was recommended as a twice daily regimen following normal tooth brushing, flossing and irrigation. Subjects were given instructions to use the cream twice daily for maintenance of healthy teeth and gums, and to apply the cream to gums with regular tooth brushing methods. They were also instructed to expectorate if necessary, but not to rinse.

The efficacy of the cream was evaluated in the following patient categories:

1) Periodontal Patients-Gingivitis
   Decreasing gingival
   Inflammation and sulcular
   Bleeding
2) Handicapped Patients
3) Denture Patients - Abrasions - Irritations - Lacerations
4) Post-Surgical Periodontal - Wound Healing Antiinfective
5) Oral Surgery Patients - Post-operative
6) Orthodontic Patients Reduce inflammation associated with banded teeth and tooth movement
7) Pedodontic Patients 13 years and under - Relieve soreness and irritation from normal exfoliation.
8) Crown and bridge patients reduce inflammation caused by abrasion, tissue irritation and soreness.
9) General dental population short term application for routine prophylaxis patient-aiding in the return to healthy gingival conditions. Useful in general restorative application to relieve irritation-soreness of dental procedures requiring the use of matrix bands, rubber dam clamps, etc.

The in vivo clinical studies showed that the dental cream prepared using the ointment base of the present invention provided an optimal combination of properties that are particularly important for dental use, including:

Safety, efficacy, and gentleness

Enhancement of tissue healing

Reduction of gingival inflammation

Reduction of bleeding

Reduction of soreness

Acceptable mint flavoring

Lack of adverse side effects

Contact virucidal activity

Efficacy against odor causing bacteria

Non-abrasive to enamel and cementum

Acceptable or no mucosal irritation or abrasion

Acceptable or no effect on taste perception

Acceptable or no alteration of the balance of the normal oral flora

Acceptable or no harm to dental restorations, bridgework, etc.

The applications and uses of dental cream for oral problems generated a uniform clinical response from all patients involved with its use. There was a generalized decrease of painful irritations, an improvement of tone and texture of gum tissue, decrease and resolve of ulcerative lesions and diminution of hemorrhagic sites. With these changes there was an over-all "feel better" attitude, and patients expressed appreciation for having the opportunity to use dental cream for their oral health problems.

EXAMPLE 3

Antimicrobial Effectiveness

The antimicrobial efficacy of the dental cream described in EXAMPLE 2 was evaluated according to the following protocol.

Preliminary testing of the dental cream was carried out using standardized strains of Staphylococcus, Pseudomonas, and *Escherichia coli*. Subsequently, cultures were obtained from the teeth and gums of volunteers, inoculated in liquid media, and allowed to grow for 48 hours. In these studies, 0.2 ml of the resultant bacterial suspension was added to two grams of the dental cream and mixed to ensure a uniform suspension of bacteria. Identical 0.2 ml aliquots of the bacterial suspensions were added to a control product that was identical in composition to the dental cream product with the exception that the control contained no microencapsulated hydrogen peroxide. The concentration of bacteria in each inoculum varied from $1 \times 10^7$ to $1 \times 10^9$ organisms per ml.

Agar pour plates were prepared by transferring 0.1 gm of each bacterial/cream suspension to a sterile 10 ml screw capped tube to which 5 ml of sterile growth medium broth was added. The resultant mixture was mixed on a vortex apparatus until completely dispersed. A series of 1:50 dilutions was prepared from this tube and labeled. A 5 ml aliquot of sterile trypticase soy broth (TSB) agar was added to each tube. The agar tubes were mixed by inversion and standard pour plates were prepared for each dilution. Plates were incubated at 37° C. Discrete colonies on each plate were counted after incubation for 24 hrs, 48 hrs and 72 hrs and reported as colony forming units (CFU's) per plate.

Under optimal conditions, the time required for the steps described above, (sample preparation, mixing and preparation of pour plates) varied from 2–4 minutes. The results of in vitro antimicrobial testing showed that 100% of all bacteria mixed into the dental cream were killed within the 2–4 minute time frame. Plates incubated for 72 hours showed no colony forming units.

In contrast, the number of bacteria that could be quantitatively recovered from an inactive control cream was determined. The inactive cream was an identical cream preparation with the exception that it contained no microencapsulated hydrogen peroxide. Results of testing carried out using Pseudomonas are shown in the TABLE I.

TABLE I

Microbial Challenge of Dental Cream Preparation

| Active CFU's/plate | | Inactive Control CFU's/plate |
|---|---|---|
| 0 | Plate Dilution #1 | Too Numerous To Count |
| 0 | Plate Dilution #2 | 12,078 |
| 0 | Plate Dilution #3 | 739 |
| 0 | Plate Dilution #4 | 23 |
| 0 | Plate Dilution #5 | 1 |

The results of in vitro testing suggest that the microencapsulation of 3% hydrogen peroxide in the dental cream product is an effective antimicrobial agent. There was initial concern that the incorporation of glycerin and other "skin protectants" in the dental cream product formulation would somehow reduce its antimicrobial efficacy. It is now clear that skin protectants can be used to protect sensitive tissues in the mouth and gums without compromising the antimicrobial efficacy of the product.

What is claimed is:

1. An ointment base useful for preparing topically applied medicament formulations, comprising a stable emulsion of at least about 10% by weight of each of water, one or more paraffins, and a liquid polyol; and less than about 10% by weight of each of beeswax, cetostearyl alcohol, a 4-hydroxy benzoic acid lower alkyl ester, a surface active agent, and a dispersing agent.

2. An ointment base according to claim 1 wherein the paraffin component includes both liquid paraffin and soft paraffin, the liquid polyol component is glycerol; the beeswax component is white beeswax; the 4-hydroxy benzoic acid lower alkyl ester component is methyl paraben, the surface active agent is polyoxyethlenesorbitan monostearate, and the dispersing agent is glyceryl monostearate.

3. An ointment base according to claim 2 having the following concentrations of ingredients, based on weight:

| | |
|---|---|
| liquid paraffin | 3 to 8% |
| white petrolatum | 5 to 15% |
| glycerol | 20 to 45% |
| white beeswax | 0.1 to 1% |
| cetostearyl alcohol | 6 to 10% |
| methyl paraben | 0.1 to 0.5% |
| polyoxyethylenesorbitan monostearate | 1 to 10% |
| glyceryl monostearate | 0.5 to 5% |
| water | to 100%. |

4. An ointment base according to claim 3 wherein the ointment base is comprised of the following ingredients, based on weight:

| | Weight % |
|---|---|
| liquid paraffin | 5 |
| white petrolatum | 10 |
| glycerol | 30 |
| white beeswax | 0.4 |
| cetostearyl alcohol | 8 |
| methyl paraben | 0.3 |
| polyoxyethylenesorbitan monostearate | 3.6 |
| glyceryl monostearate | 2 |
| purified water | to 100. |

5. An ointment base according to claim 1 wherein the paraffin component includes both liquid paraffin and soft paraffin.

6. An ointment base according to claim 5 wherein the liquid paraffin is present at a concentration of 3 to 8%, by weight.

7. An ointment base according to claim 1 wherein the liquid polyol component is glycerol.

8. An ointment base according to claim 7 wherein the glycerol is present at a concentration of 20 to 45% by weight.

9. An ointment base according to claim 1 wherein the beeswax component is white beeswax.

10. An ointment base according to claim 9 wherein the white beeswax is present at a concentration of 0.1 to 1% by weight.

11. An ointment base according to claim 1 wherein the 4-hydroxy benzoic acid lower alkyl ester component is methyl paraben.

12. An ointment base according to claim 11 wherein the methyl paraben is present at a concentration of 0.1 to 0.5% by weight.

13. An ointment base according to claim 1 wherein the surface active agent is polyoxyethlenesorbitan monostearate.

14. An ointment base according to claim 13 wherein the polyoxyethlenesorbitan monostearate is present at a concentration of 1 to 10% by weight.

15. An ointment base according to claim 1 wherein the dispersing agent is glyceryl monostearate.

16. An ointment base according to claim 15 wherein the glyceryl monostearate is present at a concentration of 0.5 to 5% by weight.

* * * * *